(12) United States Patent
Wilson et al.

(10) Patent No.: US 6,919,494 B2
(45) Date of Patent: Jul. 19, 2005

(54) **METHODS FOR TISSUE CULTURING AND TRANSFORMING ELITE INBREDS OF *ZEA MAYS* L.**

(75) Inventors: Herbert Martin Wilson, Ames, IA (US); Bruce Marvin Held, Ames, IA (US)

(73) Assignee: Stine Biotechnology, Inc., Ames, IA (US)

( * ) Notice: Subject to any disclaimer, the term of this patent is extended or adjusted under 35 U.S.C. 154(b) by 0 days.

(21) Appl. No.: 09/917,964

(22) Filed: Jul. 30, 2001

(65) Prior Publication Data

US 2002/0104131 A1 Aug. 1, 2002

Related U.S. Application Data

(63) Continuation of application No. 09/203,679, filed on Dec. 1, 1998, now Pat. No. 6,420,630.

(51) Int. Cl.[7] .......................... A01H 1/00; C12N 15/82; C12N 15/87; C12N 15/11; C12N 15/00
(52) U.S. Cl. .................... 800/294; 800/320.1; 800/320; 800/278; 536/23.1; 435/412; 435/430; 435/430.1
(58) Field of Search .................. 800/278, 294, 800/300.1; 536/23.1

(56) References Cited

U.S. PATENT DOCUMENTS 5,948,955 A * 9/1999 Holton et al.
6,162,965 A * 12/2000 Hansen

OTHER PUBLICATIONS

Bhojwani, SS et al (Developments in Crop Science, vol. 5, pp 24–41, 1983).*

* cited by examiner

*Primary Examiner*—Phuong T. Bui
*Assistant Examiner*—Georgia Helmer
(74) *Attorney, Agent, or Firm*—Jondle & Associates, P.C.

(57) ABSTRACT

The present invention is directed to methods for the tissue culture and transformation of elite inbreds of corn (*Zea mays* L.). More specifically, the present invention is directed to a method for initiating Type II callus from corn tissue. The present invention is also directed to a method for enhancing the intergration of foreign DNA in the transformation of corn using a heat shock treatment. The present invention is further directed to a method of transforming elite inbreds of corn using *Agrobacterium*.

4 Claims, No Drawings

METHODS FOR TISSUE CULTURING AND TRANSFORMING ELITE INBREDS OF ZEA MAYS L.

CROSS REFERENCE

This application is a continuation of U.S. patent application having Ser. No. 09/203,679 filed Dec. 1, 1998 that has matured into U.S. Pat. No. 6,420,630 issued Jul. 16, 2002.

BACKGROUND OF THE INVENTION

The present invention is directed to methods for the tissue culture and transformation of elite inbreds of corn (*Zea mays* L.). More specifically, the present invention is directed to a method for initiating Type II callus from corn tissue. The present invention is also directed to a method for enhancing the integration of foreign DNA in the transformation of corn using a heat shock treatment. The present invention is further directed to a method of transforming elite inbreds of corn using *Agrobacterium*.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Cells which undergo rapid division and are totipotent are generally regarded as highly suitable targets for introduction of DNA as a first step in the generation of transgenic plants. In corn, one prolific source of such cells is the so-called Type II callus (Armstrong and Green, 1985). Initiation of this type of callus has been achieved using immature embryos of certain non-elite corn inbred lines, most notably A188. Hybrid embryos with this inbred as a parent have also been used successfully. There are, however, no reports of high frequency initiation of Type II callus from immature embryos or other tissue of elite corn inbreds. Therefore, it is desired to develop a method for culturing tissue of elite corn germplasm which results in reproducible and high frequency initiation of Type II callus from elite corn germplasm.

Introduction of genes into corn can be accomplished in several ways e.g. (a) particle bombardment of cultured cells (Gordon-Kamm et al., 1990), immature embryos (Koziel et al., 1993), meristems (Lowe et al., 1995), (b) electroporation of immature embryos (D'Halluin et al., 1992), cultured cells (Laursen et al., 1994), (c) electroporation and/or polyethylene glycol treatment of protoplasts (Rhodes et al., 1988; Omirulleh et al., 1993), and (d) co-cultivation with *Agrobacterium tumefaciens* (Ishida et al., 1996; Hei and Komari, 1997; Zhao et al., 1998). *Agrobacterium tumefaciens*-mediated DNA delivery has a number of advantages. Firstly, the time taken to produce transgenic plants is short when compared to other methods. Secondly, transgenes are generally inserted as single copies, increasing the efficiency with which usable breeding material can be produced. Thirdly, high efficiencies of DNA delivery can be achieved. For breeding purposes it would be ideal to introduce genes via *Agrobacterium tumefaciens* directly into elite corn lines.

Following introduction of foreign DNA into target cells and subsequent cell division, selection is applied to identify those cells in which integration and expression of the foreign DNA is occurring. Any procedure which could increase the frequency with which foreign DNA integrates and expresses would greatly improve transformation protocols. A procedure for increasing the efficiency of integration of DNA into elite corn germplasm is described herein.

Initial methods of *Agrobacterium*-mediated corn transformation which were developed, while effective for some germplasm, do not allow for efficient transformation of elite lines. Hei et al. (European Published Patent Application No. 604 662 A1) discloses a method for transforming monocotyledons using *Agrobacterium*. In this method, plant tissues were obtained from the monocotyledon maize and the tissues were exposed to *Agrobacterium* during the tissue differentiation process. Hei et al. disclose a maize transformation protocol using maize calli. Saito et al. (European Published Patent Application No. 672 752 A1) disclose a method for transforming monocotyledons using the scutellum of immature embryos. Ishida et al. (1996) also disclose a method specific for transforming maize by exposing immature embryos to *A. tumefaciens*. The methods were optimized for inbred A188 maize lines. Transformation frequencies ranged from 12% to 30% at their highest for immature embryos from A188 lines that were 1.0–1.2 mm in length. Maize lines derived from crosses of A188 had significantly lower transformation frequencies ranging from 0.4% to about 5.3%. A188 is not generally considered a commercially useful line and Ishida et al. (1996) failed to obtain recovery of stable transformants in lines other than those containing A188.

In a subsequent method of *Agrobacterium*-mediated corn transformation (Zhao et al., 1998), efficient transformation of elite lines was possible using non-LS salt medium for the tissue culture steps, including the steps of contacting and co-cultivating immature embryos with *Agrobacterium*. The media used in this method may be based on N6 or MS salts. This method achieves high transformation frequency of hybrids between elite lines and A188 (e.g., a A188×B73 hybrid), a result which, although higher, is similar to the transformation frequency achieved in the initial transformation procedures. Although the transformation frequency of Pioneer elite inbreds (0.6–14.4%) was lower than that achieved for the hybrids, this method did result in the transformation of elite corn inbreds.

Thus, it is desired to develop methods which allow for the more efficient transformation of elite lines, i.e., methods which allow for the introduction of genes into elite corn lines at very high efficiency using *Agrobacterium tumefaciens*-mediated DNA delivery.

SUMMARY OF THE INVENTION

The present invention is directed to methods for the tissue culture and transformation of elite inbreds of corn (*Zea mays* L.). More specifically, the present invention is directed to a method for initiating Type II callus from corn tissue. The present invention is also directed to a method for enhancing the integration of foreign DNA in the transformation of corn using a heat shock treatment. The present invention is further directed to a method of transforming elite inbreds of corn using *Agrobacterium*.

In accordance with one embodiment of the present invention, Type II callus is initiated from corn tissue, preferably immature embryo, by adding a monosaccharide to the callus initiation medium. The preferred monosaccharide is glucose.

In accordance with a second embodiment of the present invention, the integration of foreign DNA into corn tissue in transformation of corn tissue is enhanced by application of a heat shock treatment following contact of the foreign DNA with the corn tissue. In a preferred embodiment, the heat shock is conducted at a temperature of 45° C. for about 30 to about 180 minutes, preferably about 30 to about 60 minutes, more preferably about 30 minutes, at a time from about 24 to about 72 hours after the contact of the DNA with the corn tissue, preferably from 48 to 54 hours.

In a third embodiment of the present invention, the transformation of elite corn inbreds is achieved at a high frequency by co-cultivating corn tissue with *Agrobacterium tumefaciens*. In one particular embodiment, the transformation of elite corn inbreds is enhanced by using *Agrobacterium* freshly grown from glycerol cultures stored at about −86° C. In a second specific embodiment, the frequency of transformation is enhanced by co-cultivating corn tissue and *Agrobacterium* at 19° C. In a third particular embodiment, the frequency of transformation is enhanced by using lower levels of cefotaxime in the culturing media In a further embodiment, the frequency of transformation of elite corn inbreds is enhanced using a combination of all of these techniques.

DETAILED DESCRIPTION OF THE INVENTION

The present invention is directed to methods for the tissue culture and transformation of elite inbreds of corn (*Zea mays* L.). More specifically, the present invention is directed to an improved method for initiating Type II callus from corn tissue. In this improved callus initiation method, the frequency of induction of Type II callus is enhanced. An enhanced frequency of Type II callus induction is achieved by including a monosaccharide, preferably glucose, as more fully described below in the callus induction medium.

The present invention is further directed to an improved method for transforming elite inbreds of corn using *Agrobacterium*. Improvements in the frequency of *Agrobacterium*-mediated corn transformation is achieved by (a) enhancing the integration of foreign DNA into corn tissue using a heat shock treatment, and/or (b) cocultivating corn tissue and *Agrobacterium* at 19° C., and/or (c) using *Agrobacterium* freshly grown from glycerol stocks stored at about −86° C., and/or (d) using a low level of cefotaxime in the culturing medium. Each of these aspects is more fully described below.

As will be discussed in more detail below, immature embryos are isolated from maize, and the immature embryos are co-cultivated with *Agrobacterium*, preferably on a solid medium. It has been found that the frequency of transformation of inbred corn lines can be enhanced during the co-cultivation step by using one or more transformation frequency enhancement techniques. These transformation frequency enhancement techniques include: (1) co-cultivating the immature embryos and *Agrobacterium* at about 19° C.; (2) using *Agrobacterium* which has been recently recovered from frozen glycerol stocks; and (3) subjecting the co-cultivated immature embryos and *Agrobacterium* to a heat shock. With respect to recently recovered *Agrobacterium*, it has been discovered that the use of *Agrobacterium* source cultures recovered from frozen glycerol stocks stored at about −86° C. and cultured on YP medium for one to two days prior to use results in an enhanced transformation frequency. For the heat shock treatment, the co-cultivated immature embryo and *Agrobacterium* are subjected to a temperature of about 35° C. to about 55° C., preferably about 40° C. to about 50° C., more preferably about 45° C. for a period of 10–180 minutes, preferably 20–90 minutes, more preferably 30–60 minutes, and most preferably 30 minutes. The co-cultivated immature embryo and *Agrobacterium* are subjected to the heat shock after 24–72 hours, preferably 24–60 hours, more preferably 48–54 hours of co-cultivation.

The Type II callus is then regenerated into plants. "Water tower" structures are generally in evidence as soon as callus is initiated from immature embryos. The desired Type II callus is cultured on solid medium to regenerate plants. The Type II callus is then regenerated into plants. Tissue containing a high frequency of "water tower" embryos structures is selected from the callus initiated from normal and "infected" immature embryos. This tissue is desirable since it allows for ready regeneration of plants. This desired Type II callus is cultured on solid medium to regenerate plants.

Following the co-cultivation period, the "infected" immature embryo is cultured, preferably on a solid medium, to initiate the generation of Type II callus. The immature embryos are incubated in the presence of at least one antibiotic known to inhibit the growth of *Agrobacterium* without the addition of a selective agent for plant transformants. It has been found that the frequency of initiation of Type II callus can be enhanced by using a staged exposure to the antibiotic. In accordance with this embodiment of the invention, the infected embryo is first cultured on a medium having a low concentration of antibiotic and then on a medium having a high concentration of antibiotic. For example, if cefotaxime is the antibiotic, the low concentration is about 15 mg/L to about 75 mg/L, preferably about 25 mg/L to about 60 mg/L, more preferably 50 mg/L, and the high concentration is about 150 mg/L to about 350 mg/L, preferably about 200 mg/L to about 300 mg/l, more preferably about 250 mg/L. It is preferred that the infected embryos are initially subjected to callus initiation without selection. Selection is added as callus initiation and Type II callus growth progresses. It has also been found that the frequency of initiation of Type II callus can be enhanced by including a monosaccharide, preferably glucose, in the initial callus initiation medium. The amount of monosaccharide which is included is about 5 g/L to about 30 g/L, preferably about 10 g/L to about 20 g/L, more preferably about 10 g/L. It has been found that the initiation of Type II callus is enhanced for normal immature embryos, as well as "infected" immature embryos.

As a first step for practicing the present invention, immature embryos are isolated from maize and exposed to *Agrobacterium*. Immature embryos are an intact tissue that is capable of cell division to give rise to callus cells that can then differentiate to produce tissues and organs of a whole plant. Immature embryos can be obtained from the fertilized reproductive organs of a mature maize plant. Exemplary methods for isolating immature embryos from maize are described by Green and Phillips (1976). Maize immature embryos can be isolated from pollinated plants, as another example, using the methods of Neuffer et al. (1982). Another method is shown in Zhao et al. (1998). The immature embryos are preferably used at approximately 8 days to 14 days after pollination, and in a particularly preferred embodiment about 9 days to about 12 days after pollination when donor plants are grown at around 25° to 30°. Preferably, the embryos exposed to *Agrobacterium* range from about 0.8 to 2.0 mm and in a particularly preferred embodiment about 1.0 mm to about 1.5 mm in size. Immature embryos are preferably aseptically isolated from the developing ear and placed in sterile medium for use.

The *Agrobacterium* used to transform the embryos is modified to contain a gene of interest. Preferably the gene is incorporated into a gene vector, to be delivered to the embryo. A variety of *Agrobacterium* species are known and *Agrobacterium* species employed for dicotyledon transformation can be used. A number of references review *Agrobacterium*-mediated transformation in monocots and dicots. These include, among others, Hooykaas (1989); Smith et al. (1995); Chilton (1993); and Moloney et al. (1993).

Many *Agrobacterium* employed for the transformation of dicotyledonous plant cells contain a vector having a DNA region originating from the virulence (vir) region of the Ti plasmid. The Ti plasmid originates from *Agrobacterium tumefaciens*. Nucleic acid containing a gene encoding a polypeptide to be expressed in maize can be inserted into this vector. Alternatively, the gene can be contained in a separate plasmid which is then inserted into the Ti plasmid in vivo, in *Agrobacterium*, by homologous recombination or other equivalently resulting processes. A vector has also been developed which contains a DNA region originating from the virulence (vir) region of Ti plasmid pTiBo542 (Jin et al., 1987) contained in a super-virulent *Agrobacterium tumefaciens* strain A281 showing extremely high transformation efficiency. The plasmid containing the gene of interest was incorporated into the virulent *Agrobacterium tumefaciens* strain A281 since strain A281 is known to have a high transformation efficiency (Hood et al., 1984; Komari et at., 1986). This type of vector is known in the art as a "superbinary vector" (see European Patent Application 0 604662A1).

Superbinary vectors are preferred vectors for the transformation methods of this invention. Exemplary superbinary vectors useful for introducing nucleic acid encoding polypeptide for expression in a maize plant via *Agrobacterium*-mediated transformation methods include the superbinary pTOK162 (as discussed in Japanese Laid-Open Patent Application No. 4-222527). This vector includes regions that permit vector replication in both *E. coli* and *A. tumefaciens*. The plasmid includes a T-DNA region, characteristic of Ti plasmids. Nucleic acid containing a gene encoding a polypeptide to be expressed in maize is inserted in the T-DNA borders. Other superbinary vectors are known and these vectors can similarly be incorporated into *Agrobacterium* (see e.g., Komari (1990) for pTOK23).

Examples of genes useful for expression in transformed plant cells are known in the art. Exemplary genes include, but are not limited to, Bt genes or patatin genes for insect resistance; the Hm1 gene and chitinase genes for disease resistance; the pat, bar, EPSP synthase gene or ALS genes for herbicide resistance; genes encoding proteins with altered nutritional properties; genes encoding enzymes involved in starch or oil biosynthetic pathways; down- or up-regulatory sequences for metabolic pathway enzymes; and the like. As those of ordinary skill in the art will recognize, this is only a partial list of possible genes that can be used with the transformation method of the present invention. Furthermore, as those of ordinary skill in the art will also recognize, regulatory sequences including promoters, terminators and the like will also be required, and these are generally known in the art. Zhao et al. (1998) discloses the construction of a prior art superbinary vector pPHP 10525. This vector contains virB, virC and virG genes isolated-from superviral strain A281. The vector includes 35Sbar and ubi/GUS plant expression cassettes inserted between the T-DNA borders. Plant expression cassettes preferably comprise a structural gene to which is attached regulatory DNA regions that permit expression of the gene in plant cells. The regulatory regions consist at a minimum of a promoter capable of directing expression of a gene in a plant cell. The promoter is positioned upstream or at the 5' end of the gene to be expressed. A terminator is also provided as a regulatory region in the plant expression cassette and is capable of providing polyadenylation and transcription terminator functions in plant cells. The terminator is attached downstream or at the 3' end of the gene to be expressed. Marker genes, included in the vector, are useful for assessing transformation frequencies in this invention.

The nucleic acid encoding a polypeptide for expression in maize is inserted into the T-DNA region of the superbinary vector using suitable restriction endonuclease recognition sites, by homologous recombination, or the like. General molecular biological techniques used in this invention are provided, for example, by Sambrook et al. (1989) and the use of homologous recombination to incorporate nucleic acid into plasmids contained in *Agrobacterium tumefaciens* is disclosed by Herrera-Esterella et al. (1983) and Horsch et al., (1984). The recombinant plasmid is selected in *Agrobacterium* based on the use of a selectable marker incorporated into the plasmid. Generally these markers are nucleic acid encoding proteins that typically confer antibiotic resistance.

Plasmids are introduced into *Agrobacterium* using methods known in the art, including the triple-cross method disclosed by Ishida et al. (1996) or the method disclosed by Zhao et al. (1998).

*Agrobacterium* containing the plasmid of interest is preferably maintained as *Agrobacterium* glycerol stocks, frozen at about −80° to −90° C., preferably about −86° C. The use of this preferred *Agrobacterium* has been found to enhance the frequency of transformation of immature corn embryos. As used in this invention the term "*Agrobacterium* capable of transferring at least one gene" refers to *Agrobacterium* containing the gene of interest, generally in a plasmid that is suitable for mediating the events required to transfer the gene to the cells to be infected. In a preferred embodiment, a sample of *Agrobacterium* is removed from the frozen glycerol stock and grown on YP medium for 0.5 to 5 days, preferably 1–2 days prior to co-cultivation with the embryos.

The concentration of *Agrobacterium* used for co-cultivation can affect the transformation frequency as shown by Ishida et al. (1996) and Zhao et al. (1998). For example, while *Agrobacterium* can transform immature embryos of maize, very high concentrations of *Agrobacterium* may also damage the immature embryos and result in a reduced callus response Ishida et al. (1996). To optimize the transformation protocol for a particular maize line, immature embryos from the maize line can be incubated with various concentrations of *Agrobacterium*. Using the protocols described in Ishida et al. (1996) and Zhao et al. (1998), the level of marker gene expression and the transformation efficiency can be assessed for various *Agrobacterium* concentrations preferably within the concentration range of about $1 \times 10^7$ to about $1 \times 10^{10}$ cfu/ml. Using these methods, and those known in the art, concentrations of *Agrobacterium* in the infection and co-cultivation step that maximize the transformation frequency for a particular maize line can be identified without undue experimentation.

Preferably, *Agrobacterium* is used for transformations in a concentration range of about $1 \times 10^8$ cfu/ml to about $1 \times 10^{10}$ cfu/ml, more preferably within the range of about $1.5 \times 10^9$ cfu/ml and still more preferably at about $0.5 \times 10^9$ cfu/ml to about $1.0 \times 10^9$ cfu/ml. Those skilled in the art will recognize that optimum *Agrobacterium* concentration ranges may vary for particular maize genotypes and for the particular *Agrobacterium* strain.

The immature embryo and *Agrobacterium* are co-cultivated in accordance with conventional techniques. In the preferred embodiment of the present invention, the isolated embryos and *Agrobacterium* are co-cultivated on solid medium. Preferably the embryos are co-cultivated with the *Agrobacterium* for a period of 2 to 5 days, more preferably 3 days. Preferably the solid medium is an LS medium, which contains MS salts. Other media can also be used such as ones which include the major inorganic salts and vitamins of MS or N6 medium, and others well known in the art. The co-cultivation may be performed at about 15° C. to about 28° C., preferably about 18° C. to about 25° C., more preferably at about 19° C. to 20° C., and most preferably at about 19° C. It has been found that co-cultivation at about 19° C. enhances the frequency of transformation.

In a preferred embodiment of the invention, the immature embryo and *Agrobacterium* are subjected to a heat shock treatment during co-cultivation. It has been found that this heat shock treatment also enhances the frequency of transformation of corn inbreds. The heat shock treatment is applied to the immature embryo and *Agrobacterium* after they have been co-cultivated for about 24 to about 72 hours, preferably for about 48 to about 54 hours. It has been found that the preferred time provides the most consistent and reproducible results. The temperature of the heat shock is from about 35° C. to about 50° C., and more preferably about 45° C. The heat shock is applied for about 20 minutes to about 90 minutes, more preferably for about 30 minutes to about 60 minutes, and most preferably for about 30 minutes.

Any one or any combination of the three techniques described above, may be used in accordance with the present invention to enhance the frequency of transformation of elite corn inbreds. In the preferred embodiment, all three techniques are used during the co-cultivation of the immature embryo and the *Agrobacterium*.

Following the co-cultivation step, the "infected" embryos are cultured to initiate the generation of Type II callus and to grow Type II callus. It is preferred to use solid medium for the initiation of callus tissue from the infected embryos. The solid medium may contain any conventional salt and vitamin mixture, such as MS salts with or without MS vitamins or other vitamins, N6 salts with or without N6 vitamins or other vitamins and the like. The solid medium also contains at least one antibiotic known to inhibit the growth of *Agrobacterium*. In this context, it is preferred to use cefotaxime as the antibiotic. It has been found that the frequency of initiation of Type II callus can be enhanced by using a staged exposure to the antibiotic. That is, the frequency of initiation of Type II callus is enhanced by exposing the infected embryos first to a low concentration of antibiotic and then a high concentration of antibiotic. When cefotaxime is the antibiotic, the low concentration is in the range of about 20 to about 100 mg/L, preferably about 30 to about 70 mg/l, more preferably about 50 mg/L and the high concentration is in the range of about 150 to about 300 mg/L, more preferably about 250 mg/L. The amount of other conventionally used antibiotics can readily be determined as described herein for cefotaxime.

It has further been found that the frequency of the initiation of Type II callus from the infected embryos is enhanced by including a monosaccharide in the solid medium. The monosaccharide is in addition to the sucrose which is conventionally present in callus initiation media. The optimum monosaccharide for a particular elite line may be determined as described herein. It is preferred that the monosaccharide is glucose, maltose, lactose, sorbitol or mannitol. It is more preferred to use glucose as the monosaccharide. The amount of monosaccharide which is included is about 5 g/L to about 20 g/L, more preferably about 10 g/L.

Any one or both of the two techniques described above, may be used in accordance with the present invention to enhance the frequency of the initiation of Type II callus during the transformation of elite corn inbreds. In the preferred embodiment, both techniques are used for callus initiation.

During the initiation and growth of Type II callus, selective pressure is applied to select for those cells that have received and are expressing polypeptide from the heterologous nucleic acid introduced by *Agrobacterium*. A selective agent is added to the solid medium on which the infected embryos are being cultured. The agent used to select for transformants will select for preferential growth of explants containing at least one selectable marker insert positioned within the superbinary vector and delivered by the *Agrobacterium*. For example, if the marker is the bar gene, it confers herbicide resistance to glufosinate-type herbicides, such as phosphinothricin (PPT) or bialaphos, and the like. Bialaphos can then be used to select for embryos that received and express the bar gene. Examples of other selective markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. In the preferred embodiment, the infected embryos are initially cultured on a solid medium which does not contain a selective agent and then transferred to medium containing a selective agent.

The initiation and growth of Type II callus free of *Agrobacterium* is obtained by the use of an antibiotic and a selective agent as described above. In accordance with a preferred embodiment of the present invention, the infected embryos are first cultured on a solid medium containing a monosaccharide, a low concentration of antibiotic and no selective agent. The culturing on this medium is performed for about 3 days to about 6 days, more preferably for about 5 days. The embryos are then transferred to a solid medium lacking glucose, containing a low concentration of antibiotic and containing a selective agent. The embryos are cultured on this medium for about 10 days to about 20 days, and more preferably for about 14 days. Adequate control of *Agrobacterium* is obtained using this protocol. It has been found that better control of *Agrobacterium* growth is then obtained by culturing the responding embryos, i.e., those embryos from which callus tissue is developing, on a solid medium containing a high concentration of antibiotic and a selective agent. This culturing is performed for about 10 days to about 20 days, and more preferably for about 14 days. Although not necessary, it is advantageous to then culture the responding embryos on a solid medium containing a low concentration of antibiotic and a selective agent for about 10 days to about 20 days, and more preferably for about 14 days. This latter culturing, if performed, is useful to identify clones and to clear up any residual *Agrobacterium* growth. The clones from either of the latter two culturings are then cultured on a solid medium containing a selective agent and no antibiotic to further grow and select the Type II callus prior to plantlet regeneration. This culturing is performed for about 10 days to about 20 days, and more preferably for about 14 days. Additional transfers on this medium may be performed as desired to achieve further growth of clonal tissue having actively growing Type II callus.

Actively growing Type II callus is selected from the clonal tissue with the objective to obtain a high frequency of "water tower" embryo structures in the cultures. The tissue containing the "water tower" embryo structures is cultured on a solid medium to mature the embryos. Maturing embryos are transferred to solid medium to further the maturation and to induce germination. Germinating embryos are transferred to solid medium for the promotion of further root and shoot development prior to final transfer to soil. The solid medium may contain any conventional salt and vitamin mixture, such as MS salts with or without MS vitamins or other vitamins, N6 salts with or without N6 vitamins or other vitamins and the like. Methods for plant regeneration are known in the art and preferred methods are provided by Kamo et al. (1985), West et al. (1993), and Duncan et al. (1985).

As discussed above with respect to the transformation method of the present invention, it has been discovered that the incorporation of a monosaccharide in the culturing medium for the induction of Type II callus results in an enhanced frequency of embryos responding. It has also been discovered that this same effect is seen when immature embryos are cultured without transformation. Thus, a further aspect of the present invention is the addition of a monosaccharide to the culture medium for initiating Type II callus. This effect is seen with any medium, including media containing MS salts and/or vitamins, N6 salts and/or vitamins and other conventional media. As described above, the monosaccharide is used in an amount of about 5 g/L to about 30 g/L, preferably about 10 g/L to about 20 g/l, more preferably about 10 g/L. The preferred monosaccharide is glucose, although other monosaccharides can be used as shown herein.

EXAMPLES

The present invention is described by reference to the following Examples, which are offered by way of illustration and are not intended to limit the invention in any manner. Standard techniques well known in the art or the techniques specifically described below were utilized.

Example 1

Improvement in the Induction Frequency of Type II Callus

Plants of the elite corn inbred Stine 963 were grown under controlled conditions, either in a grow room or in a greenhouse. Plants were exposed throughout growth to a 16 h photoperiod with a daytime temperature of around 30° C. and a nighttime temperature of around 25° C. Plants were selfed and after approximately 10 days ears were harvested. At this time the immature embryos were on average between 1.0 and 2.0 mm in length. Usually the ears were then placed at 4° for two days prior to immature embryo excision.

The response on standard N6A media (Table 1) for inducing Type II callus was variable and appeared to be dependent on the physiological state of the donor plant. The frequency of Type II callus ranged from 0% up to 95%, with an average of around 40%. Immature embryos were excised with a view to using them as targets for Agrobacterium-mediated DNA delivery. For this work a reproducible and high frequency response is required and improvement in these aspects was therefore desirable.

The protocol used for introduction of DNA mediated by Agrobacterium was based on that described by Hei and Komari (1997). The co-cultivation medium in this protocol (LSAS—Table 1) contains glucose, intended presumably as a carbon source for Agrobacterium. After close observation of immature embryos on LSAS medium it was thought worthwhile to check for the effects of glucose on culture initiation and subsequent development. 10 g/l of glucose was therefore added to N6A medium. This medium was subsequently referred to as N6AMOD (Table 1). Results of a comparison of Type II culture initiation on N6A and N6AMOD are shown in Table 2. Surprisingly, N6AMOD proved to be greatly superior to N6A in effecting Type II culture initiation from immature embryos of Stine inbred 963.

TABLE 1

Media Compositions

| Ingredients/L | N6A | N6AMOD | LSAS |
|---|---|---|---|
| MS salts[1] | | | 4.43 g |
| N6 salts[2] | 3.98 g | 3.98 g | |
| N6 vitamins[3] | 1 ml | 1 ml | |
| Na$_2$EDTA | | | 10 ml |
| Proline | 700 mg | 700 mg | 700 mg |
| Asparagine | 150 mg | 150 mg | |
| Myo-inositol | 100 mg | 100 mg | |
| 2,4-D | 1 mg | 1 mg | 1.5 mg |
| MES | 500 mg | 500 mg | 500 mg |
| Sucrose | 20 g | 20 g | 20 g |
| Glucose | | 10 g | 10 g |
| Gelrite | 2 g | 2 g | |
| Phytagar | | | 7 g |
| Acetosyringone | | | 100 μm |
| Silver nitrate | 10 mg | 10 mg | |
| pH | 6.0 | 6.0 | 5.8 |

[1]MS salts - Sigma Plant Culture Catalogue ref M 5519
[2]N6 salts - Sigma Plant Culture Calalogue ref. C 1416
[3]N6 vitamins: 2 mg/L glycine, 0.5 mg/L nicotinic acid, 0.5 mg/L pyridoxine-HCl, 1 mg/L thiamine-HCl (Chu, 1978).

TABLE 2

Effect of Glucose on Frequency of Embryos Responding

| Medium | No. of Immature Embryos Cultured | No. of Immature Embryos Responding | % Responding |
|---|---|---|---|
| N6A | 1034 | 466 | 45.1 |
| N6AMOD | 965 | 751 | 77.8 |

Various other sugars were tested in this regard (see Table 3) and some are capable of supporting an increased rate of Type II callus initiation (especially maltose, lactose, sorbitol and mannitol). None of those tested, however, were as efficient as glucose in stimulating Type II callus formation on N6A medium. All sugars were tested at 10 g/l in combination with 20 g/l sucrose.

TABLE 3

Effects of Different Sugars on Frequency of Embryos Responding

| Sugar | Embryo Response |
|---|---|
| Glucose | >75% |
| Maltose | 50%–60% |
| Lactose | 50%–60% |
| Sorbitol | 50%–60% |
| Mannitol | 50%–60% |
| Raffinose | <50% |
| Mellibiose | <50% |
| Cellobiose | <50% |
| Fructose | <50% |
| Xylose | <50% |
| Trehalose | <50% |
| Galactose | <30% |
| Control | 46% |

Similar results were achieved when glucose or other monosaccharide (which demonstrated an enhanced frequency of callus initiation in this example) is included in callus initiation media of the prior art containing other mineral salts and vitamins. Thus, the use of a monosaccharide in the callus induction medium enhances the frequency of callus induction.

Example 2

Transformation of an Elite Corn Inbred by *Agrobacterium tumefaciens*

Modifications to the protocol of Hei and Komari (1997) involving co-cultivation temperature, culture media, antibiotic concentrations and *Agrobacterium* source cultures.

*Agrobacterium* strain LBA4404 harboring "superbinary" vectors as described in U.S. patent Hei and Komari (1997) was used in corn transformation experiments. Vectors with a bar expression cassette from pBARGUS (Fromm et. al., 1990) were used to generate resistance to the herbicide bialaphos, and a gus expression cassette from pIG221 (Ohta et al., 1990) was used to produce Gus expression for transient assays. The gus expression cassette contains an intron in the N-terminal region of the gus gene which prevents expression in bacteria, but upon expression in plant cells the intron is spliced out and Gus activity is achieved (Ohta et al., 1990; Ishida et al., 1996). *Agrobacterium* containing "super binary" vectors were stored in glycerol stocks using acidified glycerol. Glycerol was acidified by adding 15 drops of 1M HCl to one liter of glycerol (Sigma G-9012). Final glycerol concentration of stocks was 15 to 20% and stocks were frozen at minus 86° C. When glycerol stocks were used as the source for transformation experiments, *Agrobacterium* was made ready for transformation experiments by removing a few flakes of frozen culture with a sterile loop, streaking it out on YP medium (5 g/l yeast extract, 10 g/l peptone, 5 g/l NaCl, and 15 g/l agar) containing 50 mg/l spectinomycin, and incubating it for one or two days at 28° C. When glycerol stocks were not used as the source, *Agrobacterium* maintained on YP plus spectinomycin at 4° C. was used to initiate new cultures of *Agrobacterium* that were grown as described above.

Co-cultivation of the immature embryos and *Agrobacterium* cells in plant transformation work has been routinely performed at 25° C. Observations by Fullner et al. (1996) suggested that better results might be expected at lower temperatures. This was confirmed by Dillen et al. (1997) for transformation of tobacco. We therefore tested 19° C. as a co-cultivation temperature for corn. Co-cultivating at 19° C. is clearly superior as indicated by transient expression of the gus gene. Subsequently, all experiments were carried out at a co-cultivation temperature of 19° C. The protocol of Hei and Komari (1997) utilizes the corn inbred line A188 and hybrids with A188. No success was reported with other inbreds (Ishida et al., 1996). Their approach was tried with Stine 963 and was not successful. Cultured immature embryos of Stine 963 treated with *Agrobacterium* after Hei and Komari, and Ishida et al produced no transformed clones. The following modifications were then tried:

(a) Stine 963 embryos, after co-cultivation on LSAS for three days, were transferred to N6A medium for production of Type II callus for subsequent selection (rather than LS 1.5D as described by Ishida et al., 1996). This allowed for at least some embryo response. 1901 embryos were co-cultivated on LSAS and then cultured and selected on N6A-based media. 3 clones were recovered from this approach (0.15%).

(b) It was noted that *Agrobacterium* growth was inhibited on media containing silver nitrate. It was also noted that 250 mg/l cefotaxime (concentration of the antibiotic used by Ishida et al to control *Agrobacterium* growth) severely inhibited embryo response. Therefore, a lower level of cefotaxime was tested in the presence of silver nitrate to see if embryo response and subsequent clone recovery could be improved. Adequate control of *Agrobacterium* growth for the first 19 day culture period after co-cultivation was obtained with 50 mg/l cefotaxime (DN62ALC (5 days) and DN62ALCB (14 days)—Table 4) but not with 10 mg/l. Further experiments indicated that it was advantageous to culture responding immature embryos on 250 mg/l cefotaxime (DN62ACB—Table 4) for 14 days after the first 14 day passage on DN62ALCB for better control of *Agrobacterium* growth. Finally, a further 14 day passage on DN62ALCB was required to identify clones and to clear up any residual *Agrobacterium* growth. The clones were then transferred to DN62B (Table 4) for growth and further selection prior to regeneration. Using this scheme less than 1% of clones identified and cultured showed any evidence of residual *Agrobacterium* growth.

The media described above (DN62ALC, DN62ALCB and DN62ACB) combine the improved survival of immature embryos with staged exposure to cefotaxime, with the improved reproducibility and high frequency of response obtained with initial exposure to glucose (on DN62ALC). With these modifications 2167 embryos were co-cultivated on LSAS and then cultured and selected on DN62ALC, DN62ALCB, DN62ACB and finally DN62ALCB. 18 clones were recovered (0.83%).

TABLE 4

Media Compositions

| Ingredients/L | DN62B | DN62ALC | DN62ALCB | DN62ACB |
|---|---|---|---|---|
| N6 salts[1] | 3.98 g | 3.98 g | 3.98 g | 3.98 g |
| N6 vitamins[1] | 1 ml | 1 ml | 1 ml | 1 ml |
| Asparagine | 800 mg | 800 mg | 800 mg | 800 mg |
| Myo-inositol | 100 mg | 100 mg | 100 mg | 100 mg |
| Proline | 1400 mg | 1400 mg | 1400 mg | 1400 mg |
| Casamino Acids | 100 mg | 100 mg | 100 mg | 100 mg |
| 2,4-D | 1 mg | 1 mg | 1 mg | 1 mg |
| Sucrose | 20 g | 20 g | 20 g | 20 g |
| Glucose | | 10 g | | |
| $AgNO_3$ | | 10 mg | 10 mg | 10 mg |
| Bialaphos | 1 mg | | 1 mg | 1 mg |
| Cefotaxime | | 50 mg | 50 mg | 250 mg |
| Gelrite | 3 g | 3 g | 3 g | 3 g |
| pH | 5.8 | 5.8 | 5.8 | 5.8 |

[1]N6 salts and vitamins: See Table 1.

(c) Certain individual experiments were noted as having produced a relatively large number of transformed clones. On further analysis, one common factor was determined to be use of *Agrobacterium* source cultures recently recovered from frozen glycerol stocks maintained at −86° C. A comparison was then made between *Agrobacterium* cells taken after one or two days culture on YP medium immediately after recovery from glycerol stocks, with *Agrobacterium* cells maintained on YP medium for a month or longer after recovery from glycerol stocks. The surprising result is noted in Table 5.

TABLE 5

| | No. of Immature Embryos Co-Cultivated | Number of Clones | % Response |
|---|---|---|---|
| YP Stocks[1] | 1530 | 25 | 1.6 |
| Glycerol Stocks[2] | 933 | 58 | 6.2 |

[1]Combined data from 10 separate experiments.
[2]Combined data from 9 separate experiments.

Example 3

Effect of Heat Shock Treatment on Integration of DNA

Use of a brief heat treatment induces a transient state of so-called 'competence' in bacteria, allowing them to take up and express DNA from a variety of sources (cited in Sambrook et al, 1989). Use of a heat shock treatment to improve transformation efficiencies in higher organisms has not been reported. It was decided to explore the possibility that a heat shock treatment could improve integration of DNA following uptake. This was investigated with *Agrobacterium*-mediated DNA delivery in the first instance. First, a heat shock treatment of 45° for 30 minutes was administered to immature embryos 21, 24, 27, and 30 hours after the initiation of co-cultivation with *Agrobacterium* on LSAS (Table 1). No enhancement of clone production was noted after 21 hours, but promising preliminary results were obtained with the longer time periods. Further experiments were then performed—the results are presented in Table 6.

TABLE 6

Effect of Heat Shock on Clone Recovery

| Heat Shock Treatment[1] | No. of Embryos Co-Cultivated | No. of Clones Recovered | % Response |
|---|---|---|---|
| (A) | | | |
| 45°/30 min/24 h | 104 | 46 | 44.2 |
| Control | 225 | 11 | 4.9 |
| (B) | | | |
| 45°/30 min/48–54 h | 208 | 120 | 57.6 |
| Control | 268 | 13 | 4.8 |

[1]Temperature and duration of heat shock at specified time after initiation of co-cultivation.

From Table 6 it can be seen that an approximately ten-fold improvement in the frequency of clone production was obtained following heat shock treatment. Although high frequencies of response could be obtained in some experiments following a heat shock treatment administered after 24 hours, more consistent and reproducible results were obtained when the heat shock was administered after 48 to 54 hours. Enhancement in frequency of clone production was also noted when the heat shock was administered for 60 minutes instead of 30.

Example 4

Regeneration of Plants

Clones could be induced to regenerate plants by the following procedures and media manipulations. Presence of the bar gene was confirmed by leaf painting with Liberty, both in the primary transformants and in progeny where Mendelian ratios were routinely observed.

(a) Actively growing Type II callus was selected from clonal tissue, with the objective of obtaining a high frequency of so-called 'water tower' embryo structures in the cultures.

(b) These tissues were then transferred to DNROB medium (Table 7). On this medium embryo maturation occurred.

(c) Maturing tissues were then transferred off DNROB after two or three weeks either to a fresh plate of DNROB or to O-INABAGS (Table 7). After a further one to two weeks, embryos with a shoot meristem were placed on MSOG medium or 1/2MSIBA (Table 7), where germination occurred. Plantlets were then transferred to tubes containing 1/2MSIBA medium for promotion of further root and shoot development prior to final transfer to soil.

TABLE 7

Media Compositions

| Ingredients/L | DNROB | O-INABAGS | MSOG | 1/2MSIBA |
|---|---|---|---|---|
| MS Salts[1] | 4.43 g | 4.43 g | 4.43 g | 2.215 g |
| Asparagine | 800 mg | | | |
| Proline | 1400 mg | | | |
| Na$_2$EDTA | 37.3 mg | 37.3 mg | 37.3 mg | 37.3 mg |
| Casamino Acids | 100 mg | | | |
| Nicotinic Acid | 0.5 mg | | | |
| Gibberellic Acid | | | 0.1 mg | |
| NAA | | 0.1 mg | | |
| Indole-3-Butyric Acid | | | | 0.1 mg |
| ABA | | 0.13 mg | | |
| Sucrose | | 60 g | 30 g | 20 g |
| Sorbitol | 20 g | | | |
| Bialaphos | 1 mg | | | |
| Gelrite | 2 g | | | |
| Phytagar | | 7 g | 7 g | 7 g |
| pH | 5.8 | 5.8 | 5.8 | 5.8 |

[1]MS Salts - Sigma Plant culture Catalogue ref. M5519.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

List of References

Armstrong, C. L. et al. (1985). "Establishment and maintenance of viable, embryogenic maize callus and the involvement of L-prline." *Planta* 164:207–214.

Chilton, M. O. (1993). *Proc. Natl. Acad. Sci. USA* 90:3119–3210.

Chu, C. C. (1978). "The N6 medium and its application to anther culture of cereal crops." In: *Proc. Symp. on Plant Tissue Culture*, Sci. Press, Beijing, pp 43–50.

D'Halluin, K. et al. (1992). "Transgenic maize plants by tissue electroporation". *Plant Cell* 4:1495–1505.

Dillen, W. et al. (1997). "The effect of temperature on *Agrobacterium tumefaciens*-mediated gene transfer to plants". *The Plant Journal* 12:1459–1463.

Duncan et al. (1985). *Planta* 165:322–332.

Fromm, M. E. et al. (1990). "Inheritance and expression of chimeric genes in the progeny of transgenic maize plants". *Biotechnology* 8:833–839.

Fullner, K. J. et al. (1996). "Pilus assembly by *Agrobacterium* T-DNA transfer genes". *Science* 273:1107–1109.

Green and Phillips (1976). *Crop Sci.* 15:417–421.

Gordon-Kamm, W. J. et al. (1990). "Transformation of maize cells and regeneration of fertile transgenic plants". *Plant Cell* 2:603–618.

Hei, Y. and Komari, T. (1997). U.S. Pat. No. 5,591,616.

Herrera-Esterella, L. et al. (1983). *EMBO J.* 2:987–995.

Hood, E. E. et al. (1984). *Bio/Tech* 2:702–709.
Hooylaas, P. J. (1989). *Plant Mol. Biol.* 13:327–336.
Horsch R. H. et al. (1984). *Science* 223:496–498.
Ishida, Y. et al. (1996). "High efficiency transformation of maize (*Zea mays* L.) mediated by *Agrobacterium tumefaciens*. *Nature Biotech.* 14:745–750.
Jin et al. (1987). *J. Bacteriol.* 169:4417–4425.
Kamo et al. (1985). *Bot. Gaz.* 146:327–334.
Komari, T. (1990). *Plant Cell Reports* 9:303–306.
Komari, T. et al. (1986). *Bacteriol* 166:88–94.
Koziel, M. G. et al. (1993). "Field performance of elite transgenic maize plants expressing an insecticidal protein derived from *Bacillus thuringiensis*". *Biotechnology* 11:194–200.
Laursen, C. M. et al. (1994). "Production of fertile transgenic maize by electroporation of suspension culture cells". *Plant Molecular Biology* 24:51–61.
Lowe, K. et al. (1995); *Biotechnology* 13:677–682.
Moloney et al. (1993). In: *Monograph Theor. Appl. Genet.*, 19:148–167, Springer Verlag, NY.
Neuffer et al. (1982). "Growing Maize for genetic purposes." In: *Maize for Biological Research* W. F. Sheridan, Ed., University Press, University of North Dakota, Grand Forks, N.Dak., pp. __.
Ohta, S. et al. (1996). "Construction and expression in tobacco of a β-glucuronidase (gus) reporter gene containing an intron within the coding sequence". *Plant Cell Physiol.* 31:805–813.
Omirulleh, S. et al. (1993). "Activity of a chimeric promoter with the doubled CaMV 35S enhancer element in protoplast-derived cells and transgenic plants in maize". *Plant Mol. Biol.* 21:415–428.
Rhodes, C. A. et al. (1988). "Genetically transformed maize plants from protoplasts". *Science* 240:204–207.
Sambrook et al. (1989). *Molecular Cloning: A Laboratory Manual*, 1989, Cold Spring Harbor Laboratory Press, Cold Spring Harbor, N.Y.
Smith, R. H. et al. (1995). *Crop Science* 35:301–309.
West et al. (1993). *The Plant Cell* 5:1361–1369.
Zhao, Z. Y. et al. (1998). International Published Patent Application No. WO 98/32326
European Published Patent Application No. 604 662 A1 (Hei et al.)
European Published Patent Application No. 672 752 A1 (Saito et al.)
Japanese Laid-Open Patent Application No. 4-222527.

What is claimed is:

1. A method for producing a corn plant comprising the steps of:
   (a) co-cultivating an immature embryo from said tissue at a temperature of about 18° C. to 20° C. with *Agrobacterium* capable of transferring at least one DNA sequence of interest to said tissue to produce an infected embryo;
   (b) culturing the infected embryo on a medium comprising an antibiotic to produce a resulting tissue;
   (c) culturing said resulting tissue on a medium comprising a selective agent and an antibiotic;
   (d) selecting transformed tissue having Type II callus; and
   (e) regenerating transgenic plants from said Type II callus.

2. The method of claim 1, wherein said temperature is about 19° C.

3. A method for transforming a line of corn comprising the steps of:
   (a) co-cultivating an immature embryo from said line with *Agrobacterium* capable of transferring at least one DNA sequence of interest to tissue of said line to produce an infected embryo;
   (b) culturing the infected embryo to initiate callus on a medium comprising an antibiotic and a compound selected from the group consisting of glucose, maltose, lactose, sorbitol and mannitol, wherein the concentration of said compound is from 5 g/L to 30 g/L;
   (c) culturing the resulting callus tissue on a medium comprising a selective agent and an antibiotic;
   (d) selecting transformed callus tissue comprising growing Type II callus; and
   (e) regenerating transgenic plants from said growing Type II callus.

4. A method for producing a transformed corn plant using *Agrobacterium* comprising the steps of:
   (a) initiating co-cultivation of an immature embryo from said tissue with *Agrobacterium* capable of transferring at least one DNA sequence of interest to said tissue to produce an infected embryo;
   (b) applying heat shock treatment during said co-cultivation;
   (c) culturing the infected embryo to initiate callus on a medium comprising an antibiotic and glucose;
   (d) culturing the resulting callus tissue on a medium comprising a selective agent and an antibiotic;
   (e) selecting transformed callus tissue having Type II callus; and
   (f) regenerating transgenic plants from said Type II callus.

* * * * *